(12) United States Patent
Ung-Chhun

(10) Patent No.: US 6,746,482 B2
(45) Date of Patent: Jun. 8, 2004

(54) METHOD FOR PRODUCING MEDICAL DEVICES AND DEVICES SO PRODUCED

(75) Inventor: Neng S. Ung-Chhun, Lincolnshire, IL (US)

(73) Assignee: Baxter International Inc., Deerfield, IL (US)

(*) Notice: Subject to any disclaimer, the term of this patent is extended or adjusted under 35 U.S.C. 154(b) by 275 days.

(21) Appl. No.: 09/991,298

(22) Filed: Nov. 9, 2001

(65) Prior Publication Data

US 2002/0198590 A1 Dec. 26, 2002

Related U.S. Application Data

(60) Continuation-in-part of application No. 09/790,395, filed on Feb. 21, 2001, which is a division of application No. 09/388,913, filed on Sep. 1, 1999, now Pat. No. 6,306,454, which is a continuation-in-part of application No. 09/211,620, filed on Dec. 15, 1998, now abandoned, which is a continuation-in-part of application No. 08/971,887, filed on Nov. 17, 1997, now Pat. No. 5,972,217, which is a continuation-in-part of application No. 08/810,751, filed on Mar. 4, 1997, now Pat. No. 5,795,483, which is a division of application No. 08/323,559, filed on Oct. 17, 1994, now Pat. No. 5,647,985.

(51) Int. Cl.[7] .................................. A61F 2/06
(52) U.S. Cl. ..................... 623/1.46; 623/1.42
(58) Field of Search ............................ 623/1.42, 1.43, 623/1.44, 1.45, 1.46, 1.47, 23.59

(56) References Cited

U.S. PATENT DOCUMENTS

| 3,945,926 A | 3/1976 | Kesting |
| 4,053,420 A | 10/1977 | Marx |
| 4,130,642 A | 12/1978 | Kikygawa et al. |
| 4,256,588 A | 3/1981 | Hoehn et al. |
| 4,283,289 A | 8/1981 | Meyst et al. |
| 4,330,410 A | 5/1982 | Takenaka et al. |
| 4,358,476 A | 11/1982 | Zimmer et al. |
| 4,399,035 A | 8/1983 | Nohmi et al. |

(List continued on next page.)

FOREIGN PATENT DOCUMENTS

| AU | 58983/90 | 1/1991 |
| EP | 0 370 584 | 5/1990 |
| EP | 0 397 403 | 11/1990 |
| EP | 0 406 485 | 1/1991 |
| EP | 0 408 462 | 1/1991 |
| EP | 0 419 346 | 3/1991 |
| EP | 0 500 472 | 9/1993 |
| EP | 0 561 379 | 9/1993 |
| JP | 03000 074 | 12/1988 |
| JP | 05034337 | 7/1991 |
| JP | 05087808 | 9/1991 |
| JP | 05148150 | 11/1991 |
| JP | 05148151 | 11/1991 |
| JP | 4-187206 | 7/1992 |
| JP | 5-194243 | 3/1993 |
| WO | 9308904 | 5/1993 |
| WO | 9303740 | 7/1993 |

OTHER PUBLICATIONS

O'Brien et al., "The Metronic Intact Xenograft: an Analysis of 342 Patients over a Seven–year Follow–up Period," *Ann. Thorac Surg.*, 1995; vol. 60(Suppl.):S253–S257.

(List continued on next page.)

*Primary Examiner*—Corrine McDermott
*Assistant Examiner*—Hieu Phan
(74) *Attorney, Agent, or Firm*—Joseph Barrett; Bell, Boyd & Lloyd LLC

(57) ABSTRACT

Medical devices and methods of producing same are provided. The medical device comprising a body member and a coating on at least a portion of the body member comprising a polyalkylene oxide and a functional group, preferably heparin, magainin, or chlorhexidine.

26 Claims, 7 Drawing Sheets

A: 2 steps coating; B: 1 step coating

U.S. PATENT DOCUMENTS

| | | | |
|---|---|---|---|
| 4,416,777 A | 11/1983 | Kuroda et al. | |
| 4,596,657 A | 6/1986 | Wisdom | |
| 4,618,533 A | 10/1986 | Steuck | |
| 4,675,361 A | 6/1987 | Ward, Jr. | |
| 4,701,267 A | 10/1987 | Watanabe et al. | |
| 4,767,541 A | 8/1988 | Wisdom | |
| 4,810,378 A | 3/1989 | Carmen et al. | |
| 4,840,851 A | 6/1989 | Gölander et al. | |
| 4,855,063 A | 8/1989 | Carmen et al. | |
| 4,915,848 A | 4/1990 | Carmen et al. | |
| 4,917,799 A | 4/1990 | Masuda et al. | |
| 4,919,823 A | 4/1990 | Wisdom | |
| 4,925,572 A | 5/1990 | Pall | |
| 4,936,993 A | 6/1990 | Nomura | |
| 4,936,998 A | 6/1990 | Nishimura et al. | |
| 4,943,287 A | 7/1990 | Carmen | |
| 4,976,861 A | 12/1990 | Pall | |
| 4,985,153 A | 1/1991 | Kuroda et al. | |
| 4,997,577 A | 3/1991 | Stewart | |
| 5,034,135 A | 7/1991 | Fischel | |
| 5,089,146 A | 2/1992 | Carmen et al. | |
| 5,092,996 A | 3/1992 | Spielberg | |
| 5,100,551 A | 3/1992 | Pall et al. | |
| 5,100,564 A | 3/1992 | Pall et al. | |
| 5,104,788 A | 4/1992 | Carmen et al. | |
| 5,128,048 A | 7/1992 | Stewart et al. | |
| 5,190,657 A | 3/1993 | Heagle et al. | |
| 5,194,145 A | 3/1993 | Schoendorfer | |
| 5,229,012 A | 7/1993 | Pall et al. | |
| 5,252,222 A | 10/1993 | Matkovich et al. | |
| 5,258,126 A | 11/1993 | Pall et al. | |
| 5,258,127 A | 11/1993 | Gsell et al. | |
| 5,647,985 A | 7/1997 | Ung-Chhun et al. | |
| 5,795,483 A | 8/1998 | Ung-Chhun et al. | |
| 6,120,491 A * | 9/2000 | Kohn et al. | 604/502 |
| 6,171,857 B1 * | 1/2001 | Hendrickson | 435/325 |
| 6,306,454 B1 | 10/2001 | Ung-Chhun et al. | |
| 6,448,054 B1 * | 9/2002 | Poznansky et al. | 424/184.1 |

OTHER PUBLICATIONS

Breillatt et al., "Recombinant Hirudin Analog Designed for Attachment to Polymers," *Abstract FASEB J.*, vol. 6:A–1320.

Gendler et al., "Toxic reactions evoked by glutaraldehyde–fixed pericardium and cardiac valve tissue bioprosthesis," *Journal of Biomedical Materials Research*, 1984, vol. 18: 727–736.

Park et al., "Chemical Modification of Implantable Biologic Tissue for Anti–Calcification," *ASAIO Journal*, 1994, vol. 40: M377–M382.

Han et al., "In Vivo Biostability and Calcification–Resistance of Surface–Modified PU–PEO–$O_3$," *Journal of Biomedical Materials Research*, 1993, vol. 27: 1063–1073.

Harasym et al., "Poly(ethylene glycol)–Modified Phospholipids Prevent Aggregation during Covalent Conjugation of Proteins to Liposomes," *Bioconjugate Chem.*, 1995; vol. 6, No. 2:187–194.

Chen et al., "Effect of 2–amino Oleic Acid Exposure Conditions on the Inhibition of Calcification of Glutaraldehyde Cross–linked Porcine Aortic Valves," *J. Biomed. Mater. Res.*, 1994; vol. 28:1485–1495.

Grimm et al., "Glutaraldehyde Affects Biocompatibility of Bioprosthetic Heart Valves," *Surgery*, 1992; vol. 111, No. 1:74–78.

Golomb et al., "The Role of Glutaraldehyde–induced Cross–links in Calcification of Bovine Pericardium Used in Cardiac Valve Bioprostheses," *Amer. J. Pathol.*, 1987; vol. 127, No. 1:122–130.

Levy et al., "Cardiovascular Implant Calcification: a Survey and Update," *Biomaterials*, 1991; vol. 12:707–714.

* cited by examiner

FIG.1
| PEO-PEO-PEO | PEO-PEO-PEO | PEO-PEO-PEO | PEO-PEO-PEO |
| ABP-ABP-ABP | ABP-ABP-ABP | ABP-ABP-ABP | ABP-ABP-ABP |
| PEO-PEO-PEO | PEO-PEO-PEO | PEO-PEO-PEO | PEO-PEO-PEO |
| ||||||||||||||||| | ||||||||||||||||| | ||||||||||||||||| | ||||||||||||||||| |
| a | b | c | d |
FIG.2
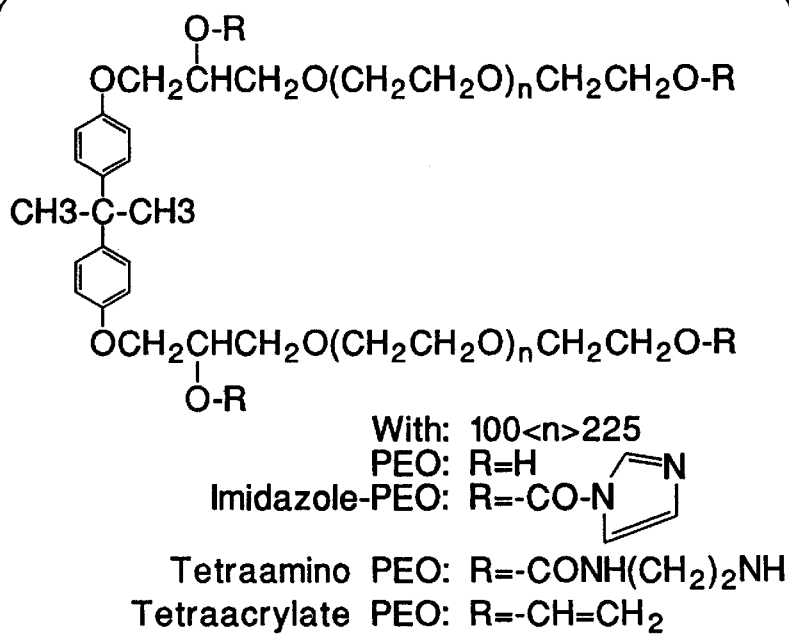
1. $CH_3O(CH_2CH_2O)_nCH_2CH_2O\text{-}R$
2. $ROCH_2CH_2O(CH_2CH_2O)_nCH_2CH_2O\text{-}R$
        PEO: R=H
    Imidazole-PEO: R=-CO-N⟨imidazole⟩
           With: 250<n>450
3. 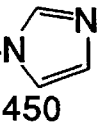
$A=CH_2=CH\text{-}COO\text{-}CH_2CH_2O(CH_2CH2O)_{77}$

METHOD FOR PRODUCING MEDICAL DEVICES AND DEVICES SO PRODUCED

CROSS REFERENCE TO RELATED APPLICATIONS

This application is a continuation-in-part of U.S. patent application Ser. No. 09/790,395, filed on Feb. 21, 2001 which is a divisional of U.S. patent application Ser. No. 09/388,913, filed on Sep. 1, 1999 now U.S. Pat. No. 6,306,454, which is a continuation-in-part of U.S. patent application Ser. No. 09/211,620, filed on Dec. 15, 1998 now abandoned, which is a continuation-in-part of U.S. patent application Ser. No. 08/971,887, filed on Nov. 11, 1997 now U.S. Pat. No. 5,972,217, which is a continuation-in-part of U.S. patent application Ser. No. 08/810,751, filed on Mar. 4, 1997 now U.S. Pat. No. 5,795,483, which is a divisional of U.S. patent application Ser. No. 08/323,559, filed on Oct. 17, 1994 now U.S. Pat. No. 5,647,985.

BACKGROUND OF THE INVENTION

The present invention relates generally to medical devices and products. More specifically the present invention relates to medical devices and products that are coated with a material to provide improved characteristics.

There are literally thousands of products that are used in the medical industry for a variety of treatments and therapies. The surface characteristics of some of these products may be critical to the ability of the products to function. Such products run the gamut from membranes used in blood and cell separation devices, theracyte devices, dialyzers, arterial filters, catheters, wound drains, vascular grafts, and heart valve tissues.

For example, a slippery or low friction surface property is required in various medical devices. These devices include wound drains, chest tubes, guide wires, catheters, and angioplasty products. A lubricious surface is desirable on these devices as it reduces pain to the patient during insertion and/or removal of the device.

Moreover, with respect to wound drains, these devices are employed in various surgical sites to remove biological fluids that can accumulate in the wound sites following surgery. Major issues with such devices can include occlusion of the lumen with clots on tissue debris. This can lead to swelling and infection. Additionally, these devices can adhere to adjacent tissue.

It is also desirable, on a number of medical products, to provide a surface that has anti-microbial properties. Likewise, medical devices that have surfaces that are non-thrombogenic are valuable in many applications.

In certain applications, it is also desirable to provide a surface that binds to certain type of cells or agents. For example, such products may be desirable for implantable biological tissue such as bioprosthetic valves.

By way of further and more detailed example, in processing whole blood for therapeutic administration to patients, it is desirable to separate the various cellular components. In particular, it is desirable to remove leukocytes because of their role in mediating immunologic reactions which can cause adverse clinical events such as allosensitization. For a review of adverse clinical sequellae to transfusion, see Sekiguchi, et al., Leucocyte-depleted blood products and their clinical usefulness, Ch. 5, pg. 26–33, from *The Role of Leucocyte Depletion in Blood Transfusion Practice* (1988). Furthermore, leukocytes are unessential for therapeutic supplementation of cell deficiencies in patients involving platelets and red cells. Thus, filter systems have been devised for passaging blood cells in order to remove leukocytes while allowing platelets or red blood to pass through for subsequent recovery.

There have been a number of approaches reported for leukocyte depletion. U.S. Pat. No. 4,330,410 discloses a packed fiber mass with leukodepletion properties comprising fibers of cellulose acetate, acrylonitrile, polyamide, or polyester. U.S. Pat. No. 4,925,572 discloses the use of a gelatin coating to inhibit red blood cell (RBC) and platelet adhesion. Leukodepletion is accomplished primarily through physical entrainment of the cells in the fiber body, and adhesion of RBCs and platelets results from the gelatin coating. U.S. Pat. No. 4,936,998 discloses a strategy for leukodepletion in which a hydrophilic monomer containing hydroxyl or amido groups and functional nitrogen-containing groups such as primary or secondary amino groups is coated onto a filter matrix of known fibers such as polyester, polyamide, etc.

Modification of fiber surfaces has also been used to obtain materials with improved cell separation properties. For example, U.S. Pat. No. 4,130,642 discloses a packed column in which the packing material comprises an Egyptian cotton which has been de-fatted and bleached so that RBC readily pass through the column.

Some separation strategies involve multiple steps. U.S. Pat. No. 4,925,572 discloses a multistep method comprising an upstream porous element for removal of gels, a second element of finer porosity for removal of aggregated matter, and a final filtration step involving common fibers to which surface tension-reducing and improved wetting are obtained by radiation grafting of biocompatible moieties. Further description of leukodepletion methods is contained in Rikumaru, et al., Advanced methods for leucocyte removal by blood filtration, Ch. 6, pgs. 35–40, from *The Role of Leucocyte Depletion in Blood Transfusion Practice* (1988).

It is of utmost importance in designing leukodepletion strategies in which one goal is to obtain good recoveries of platelets and RBCs, to achieve separations without activating platelets or complement. It is also important that any coatings utilized to enhance the separations not be leached into solution, since the recovered cells are intended for intravascular administration to patients. One approach embodies a filter composed of a porous polymer material with continuous pore structure having a coating combining a nitrogen-containing functional group with a polyethylene oxide chain having 2–15 repeating units (See Jap. Kokai Patent Application No. Hei 5 [1993]-194243). This material is said to entrap leukocytes while giving high yields of platelets.

The use of polyalkylene oxide polymers is well-known in the construction of biocompatible materials, because of its low biological activity in activating cellular and humoral components of blood, and in stimulating immune responses. However, the inertness of the polyalkylene oxide polymers may also interfere with the degree of separation that can be obtained with cell separation filters, unless combined with functional groups that enhance separation parameters. A suitable combination of coating components has not heretofore been developed which is efficacious for cell separations from whole blood as distinct from semi-purified cell suspension mixtures.

Likewise, for a number of other medical products, a suitable material or combination for coating products has not been provided.

SUMMARY OF THE INVENTION

The present invention provides improved methods for coating medical products and devices. Additionally, the present invention provides improved coated medical devices and products. More specifically, the present invention provides improved medical devices and methods of manufacturing same.

Summarizing briefly, the present invention provides, in an embodiment, medical devices which are coated, at least in part, with polyaklylene oxide and a functional group that modifies the surface properties of the device, e.g., heparin, magainin, or chlorhexidine, in a one step process. The polyaklylene oxide allows the heparin to attach to the tubing. In this regard, the polymer attaches to the surface and the heparin.

Both high and low molecular weight polyalkylene oxide compounds can be used. Low molecular weight polyaklylene oxide has a generally linear structure Y-PEO-Y and high molecular weight polyalkylene oxide compound has the general structure Y-PEO-R-PEO-Y, wherein Y is a reactive moiety selected from an oxycarbonylimidazole, tresyl-, tosyl-, N-hydroxysuccinimidyl, and p-nitrophenyl-activated esters; acrylates; glycidyl ethers; aldehydes; and amines. The oxycarbonylimidazole leaving group is preferred, as will be apparent from the detailed specification, R is a spacer molecule (a chemical backbone) consisting of either bisphenol A (4,4'-(1-methylethylidene)bisphenol) or bisphenol B (4,4'-(1-methylpropylidene)bisphenol), and PEO stands for polyalkylene oxide.

In an embodiment, the present invention provides a medical device comprising a body member and a coating on at least a portion of the body member comprising a product of a polyalkylene oxide and a functional group that modifies the surface. In an embodiment, the functional group is heparin.

In an embodiment, the functional group is chosen from the group consisting of anti-coagulants, heparin, hirudin, anti-microbial, proteins, peptides, and biopolymers.

In an embodiment, the portion of the body member is constructed at least in part from polyvinyl chloride.

In an embodiment, the portion of the body is constructed at least in part from silicone.

In an embodiment, the portion of the body is biological tissue.

In an embodiment, the coating provides a lubricious surface.

In an embodiment, the coating includes a third component.

In an embodiment, the coating provides a multilayer structure.

In an embodiment, the coating provides an anti-thrombogenic surface.

In an embodiment, the coating provides a noninflammatory surface.

In an embodiment, the coating provides an anti-bacterial surface.

In another embodiment, the present invention provides a medical device designed to be at least partially inserted into a patient comprising a body member that includes on a portion thereof a coating of a polyalkylene oxide that is cross-linked with heparin to form a coating.

In an embodiment, the coating includes water.

In an embodiment, the device is a catheter.

In an embodiment, the device is a wound drain.

In an embodiment, the device is a guide wire.

In an embodiment, the device is a chest tube.

In an embodiment, the portion thereof is constructed from silicone.

In an embodiment, the portion thereof is constructed from polyvinyl chloride.

Additionally, the present invention provides methods of providing medical devices. In an embodiment, the method comprising the steps of providing a medical device having a body and coating at least a portion of the body with a coating including a polyalkylene oxide derivative coupled to a functional group that modifies a surface property of the portion of the body.

BRIEF DESCRIPTION OF THE FIGURES

FIGS. 1a–1d illustrate alternative modes of preparing multiple layers of PEO and biopolymers onto a surface.

FIG. 2 is a schematic of the chemical structure of the polymers of a preferred embodiment.

DETAILED DESCRIPTION OF THE INVENTION

Figure 3:
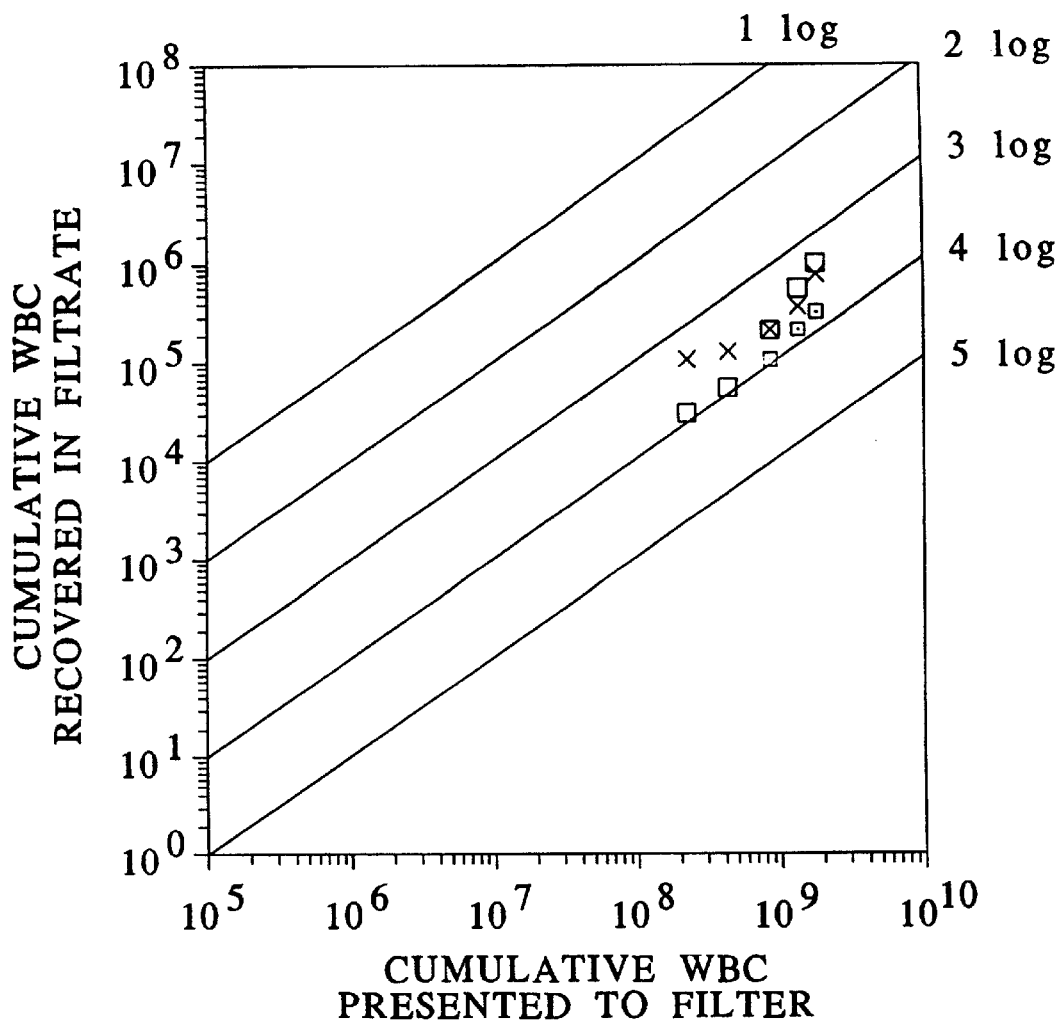
FIG. 3 illustrates the relative WBC depletion for PEO-coated and uncoated Asahi R-2000 filters. Log depletion is illustrated on the right side of the figure.
Figure 4:
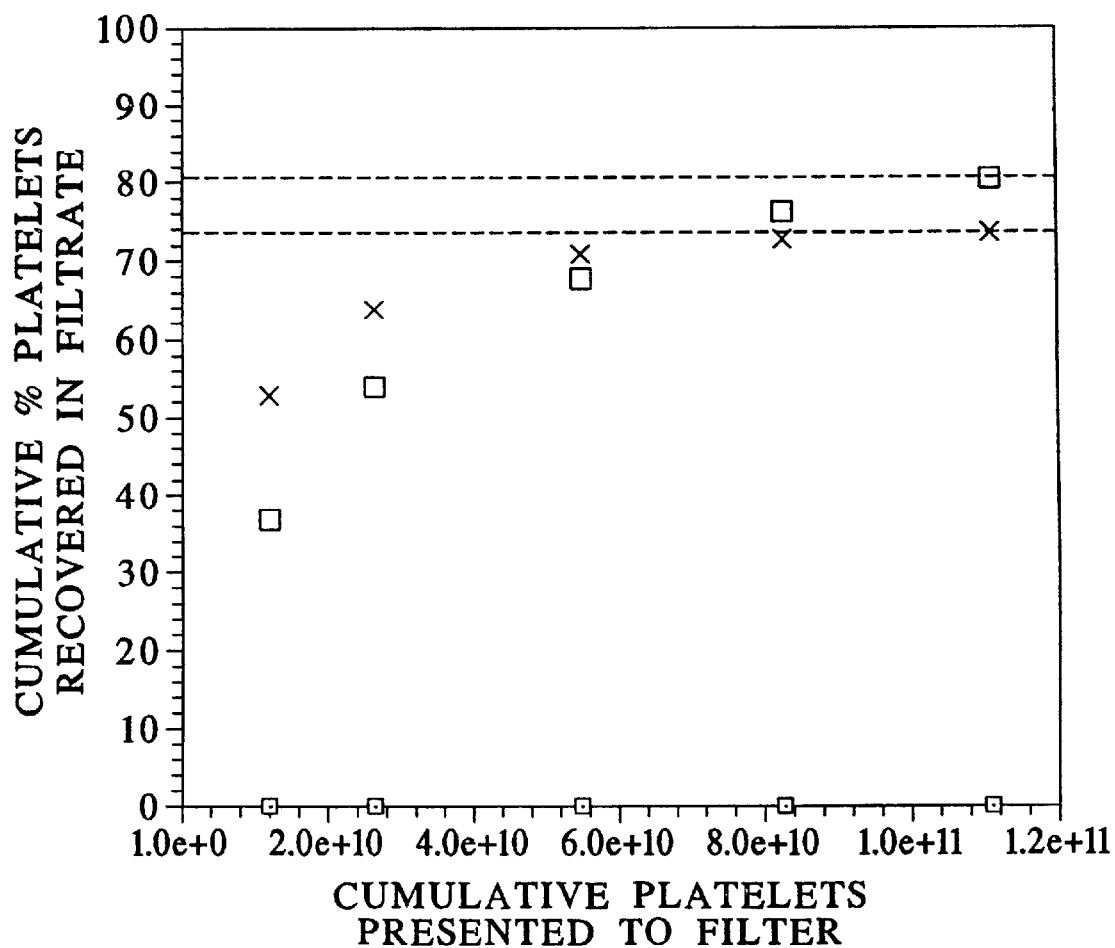
FIG. 4 illustrates the relative platelet recovery obtained with PEO-coated and uncoated Asahi R-2000 filters.

The present invention provides medical products having a coating applied thereto which changes the surface properties. Additionally, the present invention provides methods for producing such products.

Pursuant to the present invention products are provided having a surface thereof that includes a PEO cross-linked coated surface. Due to the modified PEO surface certain advantages are provided.

In an embodiment of the present invention, PEO is coupled to a functional group, preferably heparin, and then coated onto a surface of a tube. A number of advantages are achieved by this technology. For example, a simple one step process can be used to create improved medical devices such as wound-drain tubes.

Moreover, a simple coating technology process is provided that can use water as a solvent. The method produces a stable attachment of a coating to the tube that can sustain mechanical stress. It has been found that an active biopolymer (heparin) is created following its immobilization onto a surface of a tube. Thus, the production of biocompatible surfaces can be easily effected.

It has also been found that the coating can be sterilized with ETO. Such sterilization can be accomplished without losing the activity of the biopolymer. The coating can be placed on a wide variety of synthetic polymers, including polyurethane, polyethelyne, polyolefin, PTFE, metals, or metal alloys.

For example, improved bioprosthetic devices can be provided. In this regard, the PEO coating technology can be applied to various types of biological tissues, such as bovine pericardium or porcine aortic tissues, that have been chemically pre-treated with Denacol and/or glutaraldehyde for the development of bioprosthetic heart valves. The method is based on a single step process of coating a surface with PEO polymer derivatives, preferably a bis-oxycarbonyl-diimidazole-active PEO (Imz-PEO), having an average molecular weight of 20,000 daltons, and heparin.

It should be noted that the Imz-PEO-coated tissue can also be used to couple proteins, such as avidin into this matrix. This avidin-PEO-coated surface can be further employed to bind biotinylated agents, such as peptides like GREDVY, in order to produce surfaces capable of capturing endothelial cells.

PEO-coated tissues prepared by the above techniques have been shown to reduce fibrinogen binding, compared to uncoated tissue. Other potential advantages of such PEO-modified surfaces include: reduced protein adsorption; limit complement activation; eliminate protein aggregation; produce specific ligand or cell attachment sites through avidin-biotin chemistry; and intermediate activated PEO-coated-tissues can be used for attachment sites to other anti-calcification agents such as 2-amino-oleic acid or toluidine blue.

By way of further example, the surface of certain devices such as wound drains, chest tubes, guide wires, catheters, rubber septums and angioplasty products can be modified with a PEO coating to make them lubricious. To this end, such lubricious surfaces can be produced using a simple surface modification technology based on a direct coating of high molecular weight polyethylene oxide (PEO) derivatives with heparin onto polymeric tubes, using water as a solvent. The polymer materials can be varied from polyvinyl chloride (PVC) to silicone or other type of polymers that are typically used for medical devices. These materials include polyurethane, polyolefine, polyethylene, polypropylene, metal or alloy.

With respect to rubber septums, PEO and IMZ-PEO/chlorohexidine can be attached to synthetic rubber septums. This can, for example, add antimicrobial properties to the septum.

The PEO derivatives are functionalized PEO that could contain an electrophilically active compound such as oxycarbonyl-imidazoyl-PEO (Imz-PEO) or nucleophilically active such as amino-PEO ($NH_2$-PEO). This technology provides a coating that generates low-friction or lubricious surfaces which also can limit fibrinogen adsorption. It has been found that the PEO-coated PVC and PEO-coated silicone tubes are stable in saline or plasma at 37° C. for several days. Also, they can be sterilized with ETO without loss of lubricity or of low protein adsorption properties.

This technology presents several advantages including a simple coating technology that uses water as a solvent. It also allows the production of lubricious surface on PVC and/or silicone surfaces. The production of products having surfaces with low fibrinogen adsorption. It provides the availability of functional groups that allow further surface modification (e.g., coupling with anti-coagulant substances, heparin or hirudin) or anti-microbial ligand (e.g. chitosan). The technology also provides a coating that can be also sterilized with ETO (or gamma) without loss of lubricity or low protein binding ability. The technology also provides the potential application to a variety of other synthetic polymers (polyurethane, polyethylene, polyolefine, and metal or alloy).

Still further pursuant to the present invention multilayer coating can be used to provide new surface modifications. To this end, the present invention provides a new surface modification method that is based on multilayer coatings between high molecular weight PEO derivatives and anti-coagulant biopolymers containing terminal primary amine groups.

The base material can be a wide variety of materials. For example, the base material, could be derived from any biological tissue such as vascular grafts or heart valve tissues, or synthetic membranes made from various hydrophobic or hydrophilic polymers. Biopolymers containing amino-terminal groups can be derived from carbohydrate structures such as heparin (glycosaminoglycan family) and chitosan or proteins such as hirudin and magainin peptide.

FIG. 1, and specifically FIGS. 1a–1d, set forth examples of multilayer structures that can be produced. In the figures, the base material has thereon the multilayer coating. PEO refers of course to the polyethylene oxide coating discussed herein. ABP refers to the anticoagulant biopolymers.

These multiple layers of coating may provide numerous advantages. One of the advantages is to provide a permanent coating technique that assures complete coverage of the base material. Additionally, the multiple layers allow the production of a highly anti-thrombogenic surface due to the combined presence of PEO and anticoagulants (heparin or hirudin). Further, the multiple layers allow the production of a non-inflammatory (e.g. non-complement activating) material due to the presence of PEO and heparin. Still further the multilayers allow the production of a potential anti-bacterial surface because of the presence of chitosan. The multilayer coating has applicability to multiple devices, including: membranes; theracyte devices; arterial filter membranes, and oxygenators; catheters, wound drains; and vascular grafts or heart valve tissues.

In another embodiment a blood cell fractionation means is provided comprising a matrix having a fibrous structure and the matrix further characterized in having a coating applied to it which changes its surface properties with respect to cellular adherence of blood cell containing fluid coming into contact therewith. The matrix can be a packing material contained within a column, or a fibrous material compressed into a filter and held in a filter housing of conventional design and construction, although other configurations of a solid matrix contacting a fluid are within the scope of the invention. In an embodiment, the coating of polymers and the chemical reactions which are carried out to create a generally molecularly continuous polymeric surface on the matrix fibers do not require covalent or noncovalent interaction with any chemical moiety present on the native surface of the matrix, the coating itself is independent of the chemical and physical identity of the matrix. Thus, the coating is intended to be universally applicable to any filter available in the cell separation art. Examples include, without limitation, filters having a high glass content, as in glass fiber mats, filters with less or no glass content such as a filter comprising a mixture of glass and polyester, and a polyethylene terephthalate platelet filter coated with hydroxyethylmethyl-methacrylate.

Filter housings which may be conveniently used are manufactured conventionally. Examples of such housing are Swinney plastic manifolds manufactured by Gelman, pediatric Enterprise Housings, or Intermediate Enterprise Housings. The correct size correlations of filters to correspondingly suitable housings will be apparent to those skilled in the art. The only limitation applicable to the blood cell fractionation means is a surface which is incompatible with the polymer solutions. Even in the instance where molecular wetting is not obtainable with the polymer solutions, techniques utilizing emulsifiers and phase penetrants may be useful in achieving adequate coating. To Applicants' knowledge, none of the blood cell fractionation filter materials currently available commercially are to be excluded from applicability to the present invention.

In the method of separating cells using the product of the invention, a cell suspension or whole blood is filtered through the filter having the polymer coating as disclosed. The leukocytes adhere, and the platelets and RBCs pass through the in the filtrate. More generalized methods of contacting the filter with a cell containing fluid are contemplated by this invention as well. For example, contracting by passaging through a packed column, or mixing cells in bulk with dispersed matrix in solution may be employed.

As noted above, the method of the present invention is applicable to a number of products and surfaces. For example, manufacturing ease, chemical condensation reaction of the respective polymers can be carried out insitu, i.e. a first free polymer is laid down on the matrix and dried, and then the second is contacted in solution with the matrix. The ensuing reaction then produces a skin-like sheet or layer of copolymerized material at the surface or the matrix. This reaction in a preferred embodiment proceeds spontaneously at temperatures generally in the range of 5 to 200 degrees centigrade. It is evident that the time for completion of the reaction will be slightly longer at cooler temperatures than for higher temperatures in accordance with kinetic thermodynamic principles. Generally, these reactions may be carried out at cold temperatures (e.g., approximately 4° C.), as disclosed in the Examples, but very little experimentation will be required by those skilled in the art to adjust the reaction times to a particular desired temperatures of reaction.

The polymer to be contacted with the surface is a low or high molecular weight electrophilically active polyalkylene oxide. Electrophilically active means that a polyalkylene oxide polymer contains a oxycarbonyl moiety reactive with a nucleophilic center such as an amino or hydroxyl group. In a preferred embodiment, a primary amine of a biopolymer or ligand serving as a nucleophile, reacts with the carbonyl group of the imidazole-polyalkylene oxide polymer to form, upon reaction, an N-substituted carbamate bond where the carbonyl moiety from a cross-linker is incorporated into the new bond. These polymer entities may be high molecular weight, in the range of about 13,000 to 24,000 daltons, preferably about 20,000 daltons or low molecular weight about 1,000 to approximately 20,000 daltons preferably approximately 3,000 daltons. Some preferred molecules shown in FIG. 2 for reaction on surfaces will have n values of about 100–225.

The inventors have also determined that in certain applications the imidazole derived polyalkylene oxides provide excellent results, perhaps because the reaction proceeds somewhat better, or perhaps because residual unreacted groups improve leukoadhesion. In any event, Applicants do not wish to be bound to any particular theory, but disclose the result as a guide to those experienced in the art. In general, polyalkylene means polyethylene or polypropylene, since these are the most common polyalkylene oxides used in biocompatibility applications. However, Applicants consider other polyalkylene oxides up to polybutylene oxide to be within the scope of the invention.

In an embodiment, a tetra or diacrylate terminal derivative of polyalkylene oxide may be isopolymerized by first contacting with the surface, followed by irradiation with UV light or gamma rays to effect free radical polymerization. When used for blood filtration, the resulting coated filter matrix is leukodepletive with adequate recoveries of platelets and red bloods cells, but is not a efficacious as the other embodiments of the invention set forth herein.

In a method of the present invention, insitu chemical condensation between a polyalkylene oxide polymer and a biopolymer such as a glyco-protein, a protein, or a peptide can be carried out to mold the copolymer skin to the contours of the medical devices in a one-step process. In the drying step, drying in ambient air is adequate to "fix" the polymer in position, but light to moderate heat at various humidities down to less than 5% humidity or in vacuo may be applied to hasten the drying step in a manufacturing context.

The copolymerized material is highly stable to leaching, as shown in some of the Examples. In contrast to unreacted single polymer labeled with $^{125}$I which is readily leached into filtrate, the fully copolymerized material made according to a method of the present invention is highly resistant to leaching, and is stable for preparation of therapeutically acceptable cell fractions.

By way of example, and not limitation, examples of the present invention will now be given.

EXAMPLE NO. 1

In this group of examples, polyvinyl chloride and silicone tubes were coated.

1A. PEO-Coated Polyvinyl Chloride (PVC) Tubes:

PVC tubes (10 or 15 French size) were soaked in a water solution containing various concentrations of $NH_2$-PEO (1%, 2.5% or 5%). The tubes were incubated at 55° C. overnight, then they were removed. The tubes were allowed to air dry at room temperature following by another incubation at 55° C. as the curing process.

The $NH_2$-PEO-coated PVC was either used for crosslinking with another PEO derivative without further washing or was washed extensively with water to remove free PEO. Washed tubes were allowed to air dry at room temperature and stored desiccated until analysis. Note that the amount of bound PEO was estimated based on the amount of radioactive $^{125}$I-labeled-PEO tracer that was incorporated in the PEO coating solution.

1B. PEO-Coated Silicone Tubes:

Silicone tubes (15 French size) were pre-treated with sodium hydroxide before being treated with a PEO coating. The sodium hydroxide treatment consisted of soaking the tubing in 1N sodium hydroxide for 1 hour, following by extensive washing (until neutral pH) of the tubes with water.

The method of coating PEO derivatives (Imz-PEO or $NH_2$-PEO) onto silicone tubes was the same as for PVC above, except that all soaking in PEO solutions were performed at room temperature. The step that involved curing at 55° C. was omitted. The final washed tubes were stored in a desiccated vacuum.

1C. Fibrinogen Binding Assay:

All PEO or Heparin-PEO-coated tubes were tested for fibrinogen binding against control uncoated tubes. Each assay was performed with a triplicate sample using a small piece of tubing (about 0.4 cm length). Each piece of tubing was incubated in a citrate phosphate buffer (pH 7.4) containing a mixture of purified human fibrinogen and trace levels of $^{125}$I-fibrinogen. The incubation was performed at 37° C. for one hour. Unbound fibrinogen was removed by washing with phosphate buffer saline (PBS) and saline. The amount of bound fibrinogen was calculated from the specific activity of the labeled protein, and expressed as nanogram of protein per milligram of tubing or surface area.

1D. Measurement of Surface Lubricity:

Each tube was cut into about 15 lengths and was placed into a designed flow-cell filled with saline (0.9% solution). One end of the tube was connected to an Instron instrument that served to pull out the tube from the flow-cell. The maximum force required for the Instron to pull the tube out determines the surface lubricity of the tube.

The force used for pulling the control tube (uncoated PVC or silicone) was set at 20 lb. The measurement was performed at two time intervals: 1) at time zero (t=0) where the tube was pulled as soon as it was loaded into the flow-cell; and 2) at rinsed time (t=30 minutes) where the tube was allowed to stay in the flow-cell containing saline solution for 30 minutes. Then, the saline solution in the flow-cell was replaced with new saline, and finally the tube was pulled out.

1E. Stability Study of PEO-Coated PVC or Silicone:

This study was performed in saline and plasma solutions, at 37° C. up to 7 days, using $^{125}$Imz-PEO or $^{125}$I-NH$_2$-PEO-coated tubes (the radiolabeled PEO was used as a tracer). Several sets of small pieces (about 0.4 cm length) of $^{125}$I-PEO-coated PVC (or silicone), and uncoated tubes were soaked in saline or pure plasma solutions. The samples were placed on a tube rocker which allows a continuous shaking of the samples during the entire incubation period. Each set of tubes (in triplicate) was removed from the shaker after day-1 (24 hours), day-3, and day-7. Each sample was counted for total radioactivity before removal of saline or plasma solution, then it was washed twice with water. The washed piece was counted for the remaining radioactivity. The ratio between the remaining radioactivity of PEO-coated tubes after washing and the total radioactivity was recorded.

RESULTS

Figure 5:
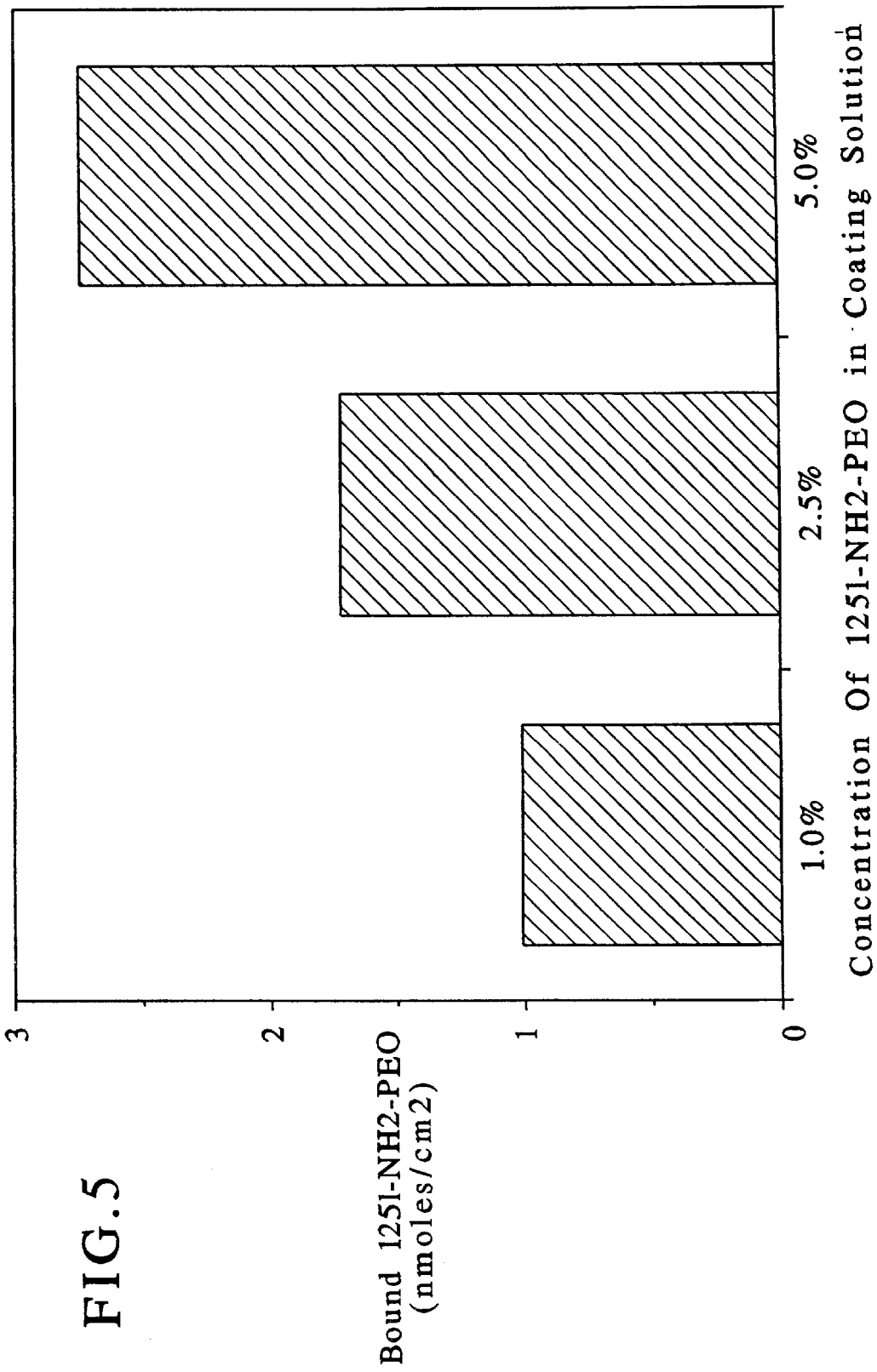
FIG. 5 illustrates the amount of amino-PEO bound to the PVC tubing versus the amino-PEO concentration in the coating solutions pursuant to Example 1A.

1A. PEO-Coated PVC:

The results of Imz-PEO or NH$_2$-PEO-coated PVC tubes are illustrated graphically in FIG. 5. FIG. 5 illustrates graphically bound NH$_2$-PEO (nmoles/cm$^2$) versus NH2-PEO concentration in the coating solution. Three solution concentrations are illustrated: 1.0%; 2.5%; and 5.0%. As shown in FIG. 5, NH$_2$-PEO appeared to bind better to the PVC tubes than the Imz-PEO derivative. Also, the amount of bound NH$_2$-PEO onto PVC increased with increasing concentration of the NH$_2$-PEO in the coating solutions. However, using high concentration of this NH$_2$-PEO (e.g. 10%) in a primary coating solution is not necessary.

Figure 6:
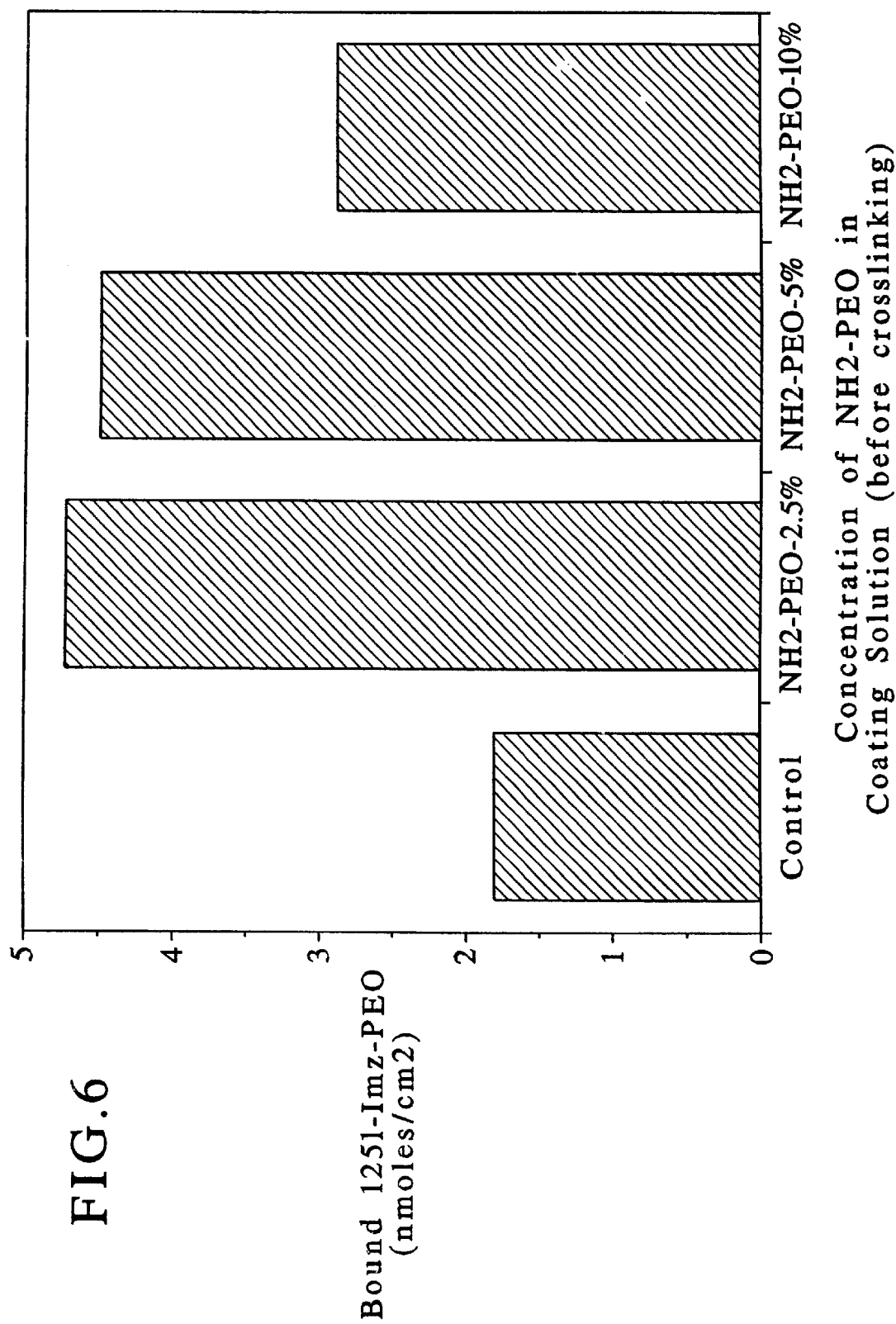
FIG. 6 illustrates the amount of bound Imz-PEO or amino-PEO coating onto a silicone tubing by a one-step process (gridded bars) pursuant to Example 1B, the shaded bars indicate a two-step process.

1B. PEO-Coated Silicone:

FIG. 6 sets forth two PEO derivatives: Imz-PEO (Imz-PEO cross-linked with NH$_2$-PEO); and NH$_2$-PEO (NH$_2$-PEO cross-linked with Imz-PEO). Illustrated in FIG. 6, both PEO derivatives were strongly bound to silicone tubing. The amount of Imz-PEO bound was about 4 fold higher than the amount of bound NH$_2$-PEO.

1C. Fibrinogen Binding:

The results of fibrinogen binding to PEO-coated PVC tubing are summarized in Tables 1, 2 and 3 below.

As shown in Table 1, PEO-coated PVC exhibited a great reduction in fibrinogen binding, compared to control uncoated PVC. Tubings coated with a low concentration of NH$_2$-PEO (1%) showed the same level of bound fibrinogen, compared to other tubings that were coated with higher concentrations of NH$_2$-PEO (2.5% or 5%).

TABLE 1

Effect Of PEO Coating On Fibrinogen Binding Onto PVC Tubing

| [NH$_2$-PEO] in coating solution | Bound Fg (ng/cm$^2$) before crosslinked (± SD) |
|---|---|
| Uncoated | 670 ± 124 |
| 1% | 85 ± 9 |
| 2.5% | 110 ± 7 |
| 5.0% | 114 ± 27 |

Also, the results in Table 2 indicated that there was no change in the level of fibrinogen binding to the PVC tubing after ETO sterilization.

TABLE 2

Effect Of ETO Sterilization On Fibrinogen Binding to PEO-Coated PVC Tubing

| PVC Tubing | Bound Fg (ng/cm$^2$) before ETO (± SD) | Bound Fg (ng/cm$^2$) after ETO (± SD) |
|---|---|---|
| Uncoated | 462 ± 43 | 394 ± 65 |
| NH$_2$-PEO (1%) | 80 ± 19 | 82 ± 26 |

Figure 7:
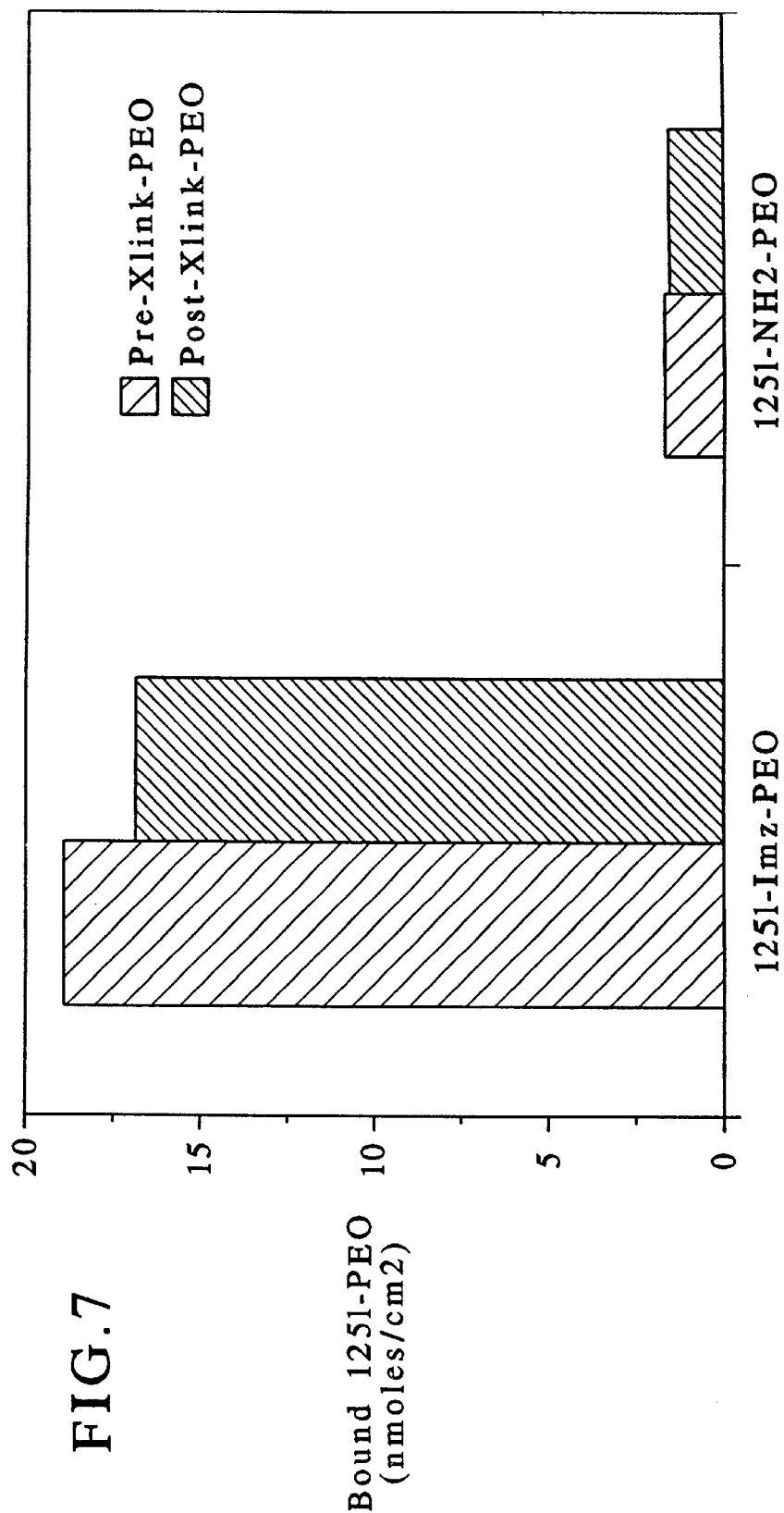
FIG. 7 illustrates graphically the effect of PEO (Pre-crosslinking, one-step) coating on fibrinogen binding to various treated silicone tubings pursuant to Example 1C.

The ability of the PEO coating to reduce fibrinogen binding was also demonstrated to be obtained with silicone (see FIG. 7). The level of fibrinogen bound to the Imz-PEO or NH$_2$-PEO-coated silicone with or without crosslinking was about the same. This result suggests that the second crosslinking reaction with Imz-PEO derivative may not be necessary in this type of coating.

TABLE 3

Effect of PEO Coating On Fibrinogen Binding Onto PVC Tubing

| Silicone Tubing & PEO Coating | Bound Fg (ng/cm$^2$) Pre-Crosslinked (± SD) |
|---|---|
| Uncoated | 258 ± 173 |
| $^{125}$I-Imz-PEO | 82 ± 27 |
| $^{125}$I-NH$_2$-PEO | 62 ± 19 |

Figure 8:
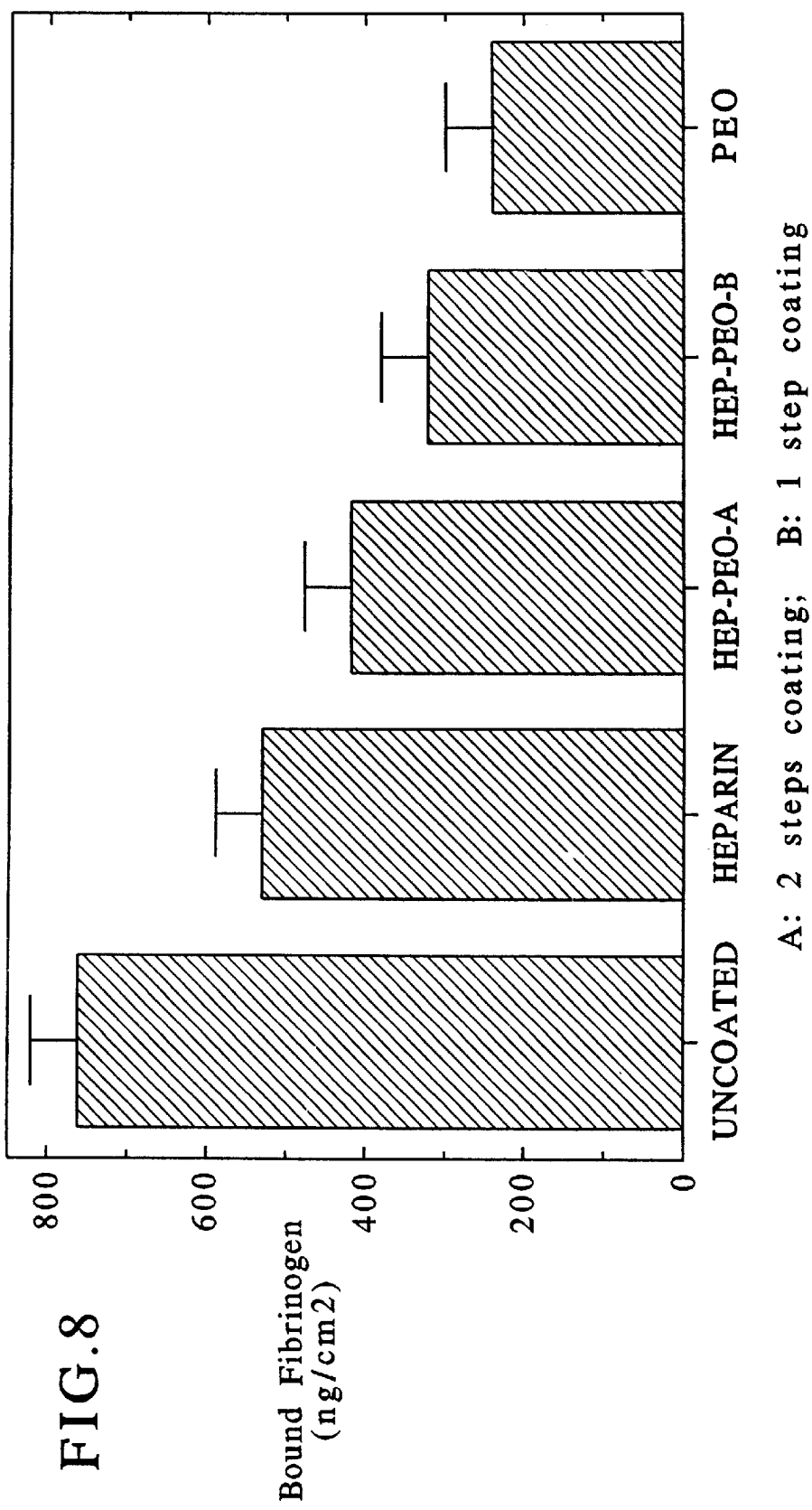
FIG. 8 illustrates the effect of heparin coating on fibrinogen binding to various treated silicone tubings pursuant to Example 2.

However, Imz-PEO coating may be used as crosslinker reagent to the attachment of heparin, as shown in FIG. 8. The results in FIG. 8, indicated that heparin and Imz-PEO can be incorporated onto silicone tubing by a one step (S1) or two step (S2) processes to produce low fibrinogen binding surface.

1D. Surface Lubricity:

The results of the effect of PEO coating on tubing lubricity are summarized in Tables 4 and 5 below for PVC and silicone, respectively.

In this analysis, surface lubricity was measured by applying a maximum force to pull out the tube from the flow-cell filled with saline solution. The force for the control uncoated was set at 20 lb, on the Instron instrument.

TABLE 4

Effect Of PEO-Coated PVC On Tubing Lubricity

| PVC (10 fr.) | Pre-ETO (t = 0) | Pre-ETO (t = 30 min.) | Post-ETO (t = 0) | Post-ETO (t = 30 min.) |
|---|---|---|---|---|
| Experiment #1 (n = 3) NH2-PEO (1%) | not done | 7.6 ± 4.3 | not done | 2.6 ± 0.6 |

TABLE 4-continued

Effect Of PEO-Coated PVC On Tubing Lubricity

| PVC (10 fr.) | Pre-ETO (t = 0) | Pre-ETO (t = 30 min.) | Post-ETO (t = 0) | Post-ETO (t = 30 min.) |
|---|---|---|---|---|
| Experiment #2 (n = 1) S1 (NH2-PEO 1%) | 0.75 | 0.56 | 0.89 | 0.94 |

TABLE 5

Effect Of PEO-Coated Silicone On Tubing Lubricity Measured by friction test. Control uncoated = 20 lb

| Silicone (15 fr.) (n = 2) | (t = 0) | (t = 30 min.) |
|---|---|---|
| Imz-PEO | 13.6 ± 9.0 | 4.4 ± 1.3 |
| NH2-PEO | 5.7 ± 3.4 | 2.4 ± 0.2 |

The forces required for pulling the PEO-coated PVC or silicone tube were much lower than the force necessary for the uncoated materials. For both initial force (t=0) or rinsed force (t=30 minutes) PVC tubing coated with 1% $NH_2$-PEO solution showed the same degree of lubricity, compared to other coatings (Table 4). These results suggest that $NH_2$-PEO can be used at low concentration (1%) as a single coating onto PVC tubing.

Similar results were also observed with $NH_2$-PEO-coated silicone tubing (Table 5). This derivative by itself can be used alone for coating silicone tube to produce surface with low-friction and low fibrinogen binding.

1E. Stability of PEO Coating:

A. PVC Tubing:

The results of the stability study of PEO-coated PVC tubing in saline and in plasma are summarized in Tables 6 and 7, respectively. As set forth in Table 6, all PEO-coated PVC with or without additional cross linking are very stable in saline solution, at 37° C. up to 7 days.

TABLE 6

Stability of $^{125}$I-PEO-Coated PVC Tubing in Saline Solution at 37 C.

| PVC Tubing | % Of Recovery Day-1 (Å SD) | % Of Recovery Day-3 (Å SD) | % Of Recovery Day-7 (Å SD) |
|---|---|---|---|
| $^{125}$I-$NH_2$-PEO-1.0% | 95 ± 9 | 90 ± 9 | 98 ± 2 |
| $^{125}$I-$NH_2$-PEO-2.5% | 94 ± 7 | 94 ± 3 | 93 ± 5 |
| $^{125}$I-$NH_2$-PEO-5.0% | 91 ± 6 | 93 ± 4 | 96 ± 3 |

Also, these tubings (post saline incubation) showed very good reduction in fibrinogen binding compared to control uncoated tubing (see Table 7 below).

TABLE 7

Stability of $^{125}$I-PEO-Coated PVC Tubing in Saline Solution at 37° C.: Effect On Fibrinogen Binding

| PVC Tubing | Bound Fg (ng/cm2) Day-1 (± SD) | Bound Fg (ng/cm2) Day-3 (± SD) | Bound Fg (ng/cm2) Day-7 (± SD) |
|---|---|---|---|
| Uncoated | 576 ± 45 | 513 ± 53 | 561 ± 44 |
| $^{125}$I-$NH_2$-PEO-1.0% | 75 ± 9 | 76 ± 16 | 71 ± 13 |
| $^{125}$I-$NH_2$-PEO-2.5% | 119 ± 20 | 100 ± 25 | 100 ± 18 |
| $^{125}$I-$NH_2$-PEO-5.0% | 87 ± 9 | 101 ± 8 | 93 ± 19 |

However, in pure human plasma, the percentage of the recovery of bound $NH_2$-PEO is in the range of 60% to 90% depend on the initial coating concentrations and the duration of the incubation (see Table 8 below).

TABLE 8

Stability Of $^{125}$I-PEO-Coated PVC Tubing in Human Plasma at 37° C.

| PVC Tubing | % Of Recovery Day-1 (± SD) | % Of Recovery Day-3 (± SD) | % Of Recovery Day-7 (± SD) |
|---|---|---|---|
| $^{125}$I-$NH_2$-PEO-1.0% | 92 ± 2 | 77 ± 10 | 65 ± 5 |
| $^{125}$I-$NH_2$-PEO-2.5% | 86 ± 5 | 77 ± 20 | 72 ± 1 |
| $^{125}$I-$NH_2$-PEO-5.0% | 102 ± 27 | 79 ± 5 | 72 ± 4 |

B. Silicone Tubing:

Similar results were obtained with PEO-coated silicone tubing. In saline the coating is very stable, the percentage of PEO recovery was all above 95% (see Table 9 below).

TABLE 9

Stability Of $^{125}$I-PEO-Coated Silicone Tubing in Saline Solution at 37° C.

| Silicone Tubing | % Of Recovery Day-1 (± SD) | % Of Recovery Day-3 (± SD) | % Of Recovery Day-7 (± SD) |
|---|---|---|---|
| $^{125}$I-$NH_2$-PEO | 101 ± 1 | 102 ± 3 | 102 ± 5 |
| $^{125}$I-Imz-PEO | 100 ± 1 | 100 ± 6 | 99 ± 5 |

After saline incubation, all PEO-coated silicone tubing still showed good reduction in fibrinogen binding (see Table 10 below).

TABLE 10

Stability Of $^{125}$I-PEO-Coated Silicone Tubing in Saline Solution at 37° C.: Effect On Fibrinogen Binding

| Silicone Tubing | Bound Fg (ng/cm2) Day-1 (± SD) | Bound Fg (ng/cm2) Day-3 (± SD) | Bound Fg (ng/cm2) Day-7 (± SD) |
|---|---|---|---|
| $^{125}$I-$NH_2$-PEO | 84 ± 21 | 68 ± 24 | 89 ± 17 |
| $^{125}$I-Imz-PEO | 103 ± 43 | 99 ± 57 | 102 ± 7 |

In plasma and up to 7 days incubation at 37° C., PEO-coated silicone tubes are very stable, since the percent recovery of bound PEO varied between 80 and 100% (see Table 11 below).

TABLE 11

Stability Of $^{125}$I-PEO-Coated Silicone Tubing in Human Plasma at 37° C.

| Silicone Tubing | % Of Recovery Day-1 (± SD) | % Of Recovery Day-3 (± SD) | % Of Recovery Day-7 (± SD) |
|---|---|---|---|
| $^{125}$I-$NH_2$-PEO | 84 ± 2 | 84 ± 7 | 80 ± 7 |
| $^{125}$I-Imz-PEO | 99 ± 3 | 94 ± 1 | 91 ± 4 |

EXAMPLE NO. 2

1. Attachment of Heparin onto Silicone Materials:

All silicone materials were pre-treated with sodium hydroxide before coating. The sodium hydroxide treatment consisted of soaking the tubing in sodium hydroxide (1N) for 1 hour, following by extensive washing with water until neutral pH. PEO derivatives (Imz-PEO or $NH_2$-PEO) of low (about 3,400 daltons) and high (about 20,000 daltons) molecular weights were used in these experiments.

Heparin and Imz-PEO were incorporated onto the silicone matrix by either reacting heparin with Imz-PEO-coated silicone tubes (a two steps process), or by mixing Imz-PEO and heparin in the same solution (one step process).

Method A (One Step):

Silicone pieces were incubated in a water solution mixture containing Imz-PEO and sodium heparin at room temperature for up to 2 days. Coated silicone pieces were air-dried, and kept under house vacuum overnight.

Method B (Two Steps):

Silicone pieces were soaked in an Imz-PEO solution (2%) at 4° C. for overnight. The silicone pieces were removed and air-dried, then they were incubated in a water-solution containing heparin. The incubation was performed at 4° C. for up to 2 days. Silicone pieces were washed and treated as described above. The ability of heparin or PEO-heparin to coat silicone surface was evaluated with a direct fibrinogen binding assay as described in Example No. 1C.

2. Anti-Fibrinogen Binding Assay:

This assay was performed following an exposure of silicone materials with fresh whole blood.

Whole Blood Incubation:

Fresh whole blood was obtained from three normal donors by venipuncture, anti-coagulated with heparin at a final concentration of 1 U/ml. One millimeter of whole blood was added to each silicone test article (coated and uncoated, in triplicate), and was incubated at 37° C. for 60 minutes. Silicone samples obtained after whole blood incubation were removed and washed immediately with PBS (2.0 ml×3 times), and fixed with 1% paraformaldehyde. These samples were stored at 4° C. for at least 24 hours until analyzed for fibrinogen adsorption.

Anti-Fibrinogen Binding Assay:

Paraformaldehyde fixed silicone samples were washed with PBS (1 ml×2) and citrate phosphate buffer (CPB) which was composed of $NaH_2PO4$ (0.01M), Na citrate (0.01M), NaI (0.01M) and 0.02% $NaN_3$ (pH 7.4). The materials were then, soaked in CPB containing $^{125}$I-anti-human fibrinogen monoclonal antibody, at room temperature for 60 minutes. Unbound protein was removed by washing extensively with PBS, saline and water. The amount of fibrinogen bound was calculated from the specific activity of the labeled antibody and expressed as nanogram of anti-fibrinogen per surface area.

3. Assay for Catalytic Activity of Bound Heparin:

The activity of immobilized-heparin was analyzed with Chrom Z-heparin kit (obtained from Helena Laboratories). This test kit determines the amount of active heparin in a sample by measuring residual factor Xa activity following incubation of the heparin samples with anti-thrombin III and factor Xa (in excess). Small pieces of heparin-coated silicone test articles were incubated with the solutions of the test kit. A calibration curve was made from samples containing heparin standards and pieces of control uncoated-silicone.

Results:

1. Attachment of Heparin onto Silicone Materials. Fibrinogen Binding Assay:

The results of this assay are illustrated in FIG. 8. PEO-Heparin coating by a one step coating process (FIG. 8, HEP-PEO-B) showed slightly better reduction in fibrinogen binding to the surface indicating that PEO-Heparin-coated surface prepared by a one step coating appeared to produce more active surface than a two step coating (FIG. 8, HEP-PEO-A).

2. Anti-Fibrinogen Binding Assay:

The results of heparin and Imz-PEO attachment onto silicone tubing by a one step process to produce a low fibrinogen binding surface from fresh whole blood were summarized in Table 12.

TABLE 12

Binding of fibrinogen from whole blood onto PEO/Heparin-coated silicone surfaces (ng/cm2)

| Silicone | Donor-1 | Donor-2 | Donor-3 | Average ± SD |
|---|---|---|---|---|
| Uncoated | 10.57 | 9.7 | 4.77 | 8.35 ± 3.13 |
| PEO/Heparin | 2.64 | 3.97 | 3.48 | 3.36 ± 0.67 |

3. Heparin Catalytic Activity Assay:

The results of catalytic activity assay of PEO-heparin-coated silicone prepared by a one step coating procedure are summarized in Table 13.

TABLE 13

Heparin Activity After Immobilization Onto Silicone Surfaces

| Silicone Samples | Activity (mu/cm2) |
|---|---|
| Uncoated | 0.39 |
| PEO/Heparin | 1.59 |

EXAMPLE NO. 3

3A. Coating Silicone Tubing with Magainin II (MG) Peptide:

Silicone tubing was cut into multiple sections of approximately ¼ inch per section. Each section was placed in each well of a 96-well polyfiltronic plate for up to a total of 40 wells. Two different types of coating solutions containing MG/$^{125}$I-MG (20 ug/ml) and Imz-PEO-3K (1%) was added to each well of the first set of 20 wells, and a solution containing MG/$^{125}$I-MG (20 ug/ml) and Imz-PEO-20K (1%) was added to the last set of 20 wells. The specific activity of the MG solution was approximately 2000 cpm/ul solution. The entire plate was incubated at 4° C. for up to 72 hours, and then each set of 20 coated-samples was removed and combined into one vial. Each vial was then washed extensively with phosphate buffered saline (PBS, pH 7.4) to remove unbound peptide. The amount of bound MG was determined from counting the washed samples for remaining radioactivity ($^{125}$I-MG). Coated samples were dried with nitrogen, and stored at 4° C.

Results:

The results of these experiments are summarized in Table 14. The amount of bound magainin was determined by counting bound $^{125}$I-MG in a pool of 20 pieces of coated samples per set. The binding of magainin to the silicone tubing was about the same for each type of PEO.

TABLE 14

Attachment of Magainin II on Silicone Tubing

| Coatings | Bound-MG (ug/cm2) |
|---|---|
| MG/PEO-3K | 0.123 |
| MG/PEO-20K | 0.107 |

3B. Stability of Magainin-Coated Silicone Tubing in Human Serum:

$^{125}$I-MG coated-samples were incubated in human serum solution (~0.5 ml of serum/silicone piece) at 4° C. After each time interval (24, 48 and 72 hours), the entire vial containing serum and tubing sample was removed and counted with a gamma counter, before washing. The amount of count before washing was used as control or Pre-incubated sample (Pre-sample). Following counting, the serum was discarded and each tubing section was washed extensively with saline to remove unbound MG. Then, the remaining radioactivity on the washed sample (post-sample) was counted. The percent of recovery was determined from the ratio of radioactivity found between pre and post-incubated samples.

Results:

The average percent of recovery of each type of PEG/magainin-coated samples varied from 78 to 91% for up to 72-hrs incubation (Table 15). These results suggest that all coatings were very stable following an exposure to human serum at 4° C. for up to 72 hours.

TABLE 15

Recovery of $^{125}$I-Magainin-Coated Silicone Samples in Human Serum (Results are expressed as % of pre-incubated samples, n = 3)

| Coatings | Day-1 (24 hrs) | Day-2 (48 hrs) | Day-3 (72 hrs) |
|---|---|---|---|
| MG-PEO-3K | 91 ± 21 | 83 ± 2 | 78 ± 5 |
| MG-PEO-20K | 88 ± 2 | 86 ± 1 | 78 ± 5 |

EXAMPLE NO. 4

4A. Coating of Silicone Tubing with Chlorhexidine (CLX):

Two sets of coating solutions containing a mixture of chlorhexidine and $^{14}$C-Chlorhexidine (approximately 2000 to 2500 dpm/ul) were prepared. Each set contained 4 different levels of CLX concentrations of approximately 1, 2, 5, and 10%. Imz-PEO-20K (1%) was added to the second set of the coating solutions. Silicone tubing was cut into multiple ½ inch sections, and each section was further sliced longitudinally in half. Then, they were incubated in each corresponding coating solution (3 pieces/ml). The entire reaction mixtures were further placed on a plate rocker at room temperature for overnight (approximately 15 hours). The resulting coated-samples were removed from each coating solution, and washed twice with 1.0 ml, and 0.5 ml of deionized water. Each group of 3 coated pieces was divided into sub-groups of one piece, and two pieces. The sub-groups containing one coated piece were used for assessing the binding of chlorhexidine: each piece was placed in a scintillation vial containing 10.0 ml scintillation fluid, and counted using a beta counter. The other sub-group containing two coated pieces, per coating solution, was air-dried and stored under dark at room temperature. These dried samples were used for stability assessment.

Results:

The results of these experiments are summarized in Table 16. The amount of CLX bound to silicone tubing, determined by using $^{14}$C-CLX in the coating solution, appeared to increase proportionally to the concentrations of CLX in the coating solution. The presence of Imz-PEO in the coating solution did not appear to affect the binding of chlohexidine to the tubing. It was suspected that the washing of unbound CLX was not complete.

TABLE 16

Binding of Chlorhexidine (CLX) onto Silicone Tubing (n = 2), expressed as (ug/cm2)

| Coating solutions | Bound-CLX (without PEO) | Bound CLX with PEO (1%) |
|---|---|---|
| CLX-1% | 3.02 ± 0.28 | 1.63 ± 0.26 |
| CLX-2% | 3.61 ± 3.37 | 3.09 ± 0.37 |

TABLE 16-continued

Binding of Chlorhexidine (CLX) onto Silicone Tubing (n = 2), expressed as (ug/cm2)

| Coating solutions | Bound-CLX (without PEO) | Bound CLX with PEO (1%) |
|---|---|---|
| CLX-5% | 4.17 ± 0.39 | 4.13 ± 0.62 |
| CLX-10% | 15.42 ± 13.23 | 5.96 ± 0.26 |

4. B. Stability of $^{14}$C-Chlorhexidine (CLX)-Coated Silicone Tubing:

Briefly, the remaining dried 2 pieces of $^{14}$C-CLX-coated silicone samples (6A) were further cut into a total of 4 pieces (each piece in half). Then, each new piece (up to 3 pieces) was incubated in a microcentrifuge tube containing human serum (0.5 ml per piece) while the $4^{th}$ piece was not exposed to serum, but saved and used as control sample (Pre-incubated sample). Following incubation, $^{14}$C-CLX-coated samples were removed from the serum media, at 24 hours, 48 hours, and 72 hours, then washed with water to remove unbound CLX. Each washed $^{14}$C-CLX-sample was directly placed in each corresponding scintillation vial (n=1), and counted for remaining radioactivity with a beta counter, along with the control sample (Pre-sample). The percent of recovery was determined by taking a ratio between the amount of counts (dpm) of sample after exposure (Post-sample) to serum and sample before serum exposure (Pre-sample).

Results:

The results of the stability or desorption of chlorhexidine ($^{14}$C)-coated silicone tubing samples are summarized in Table 17. The overall recovery of CLX-coated silicone tubing (n=1) after 24, 48, and 72 hours following an incubation in human serum, varied drastically from as low as 41% (CLX 10%, 72 hrs incubation) to 80% (CLX-10%, 24 hrs incubation). The recovery of the CLX coating in serum appeared to be independent of the amount of CLX bound to the silicone surface, and the duration that the samples were exposed to serum. At low concentration of CLX, the presence of Imz-PEO in the coating solution (1% CLX) appeared to slightly enhance the recovery of CLX after serum incubation, compared to the recovery of CLX in samples prepared without Imz-PEO. However, the overall low recovery of CLX-coated samples may be due to the incomplete removal of unbound CLX. An improved washing procedure need to be explored to assure the complete removal of unbound CLX.

TABLE 17

Recovery of $^{14}$C-Chlorhexidine-Coated Silicone Samples in Human Serum (Expressed as % of Pre-incubated sample, n = 1)

| Bound CLX-Recovery (as % of Pre) | Day-1 (24 hrs) W/O Imz-PEO | With Imz-PEO | Day-2 (48 hrs) W/O Imz-PEO | With Imz-PEO | Day-3 (72 hrs) W/O Imz-PEO | With Imz-PEO |
|---|---|---|---|---|---|---|
| CLX-1% | 52 | 65 | 60 | 62 | 47 | 67 |
| CLX-2% | 43 | 59 | 44 | 51 | 46 | 51 |
| CLX-5% | 53 | 48 | 48 | 55 | 51 | 59 |
| CLX-10% | 80 | 64 | 67 | 46 | 41 | 48 |

EXAMPLE NO. 5

5A. Attachment of PEO, or PEO Derivatives onto Chlorinated Rubber Septums:

Chlorinated rubber septums were incubated at 60° C. in water solution containing PEOs or PEO derivatives (amino-PEO, acrylate-PEO) at various concentrations (20%, 10% and 5%). The septums were removed, air dried and cured at 60° C. for another hour. Then, coated-septums were washed extensively with water to remove unbound PEOs. Washed septums were air dried, and ready for further analysis.

In some experiments PEO or PEO derivatives were radiolabeled with $^{125}$I-Na. The $^{125}$I-PEO was mixed with non-labeled-PEO and the solution mixture was used for coating onto septums. The amount of bound PEO was calculated from the specific activity of the labeled PEO, and expressed as micro-gram of PEO per gram of septum.

5B. Fibrinogen Binding Assay:

PEO-coated and uncoated-septums were incubated in a citrate phosphate buffer (pH 7.4) containing a mixture of purified human fibrinogen and trace levels of $^{125}$I-fibrinogen. The incubation was performed at 37° C. for one hour. Unbound fibrinogen was removed by washing with PBS and saline. The amount of bound fibrinogen was calculated from the specific activity of the labeled protein, and expressed as nanogram of protein per milligram of septum.

5C. Stability Study of PEO-Coated Septum:

This study was performed in saline solutions, at room temperature up to 10 days, using $^{125}$I-PEO or $^{125}$I-NH$_2$-PEO-coated septums (the radiolabeled PEO was used as a tracer). Saline solution was replaced each 3 to 4 days. Several sets of coated-septums (each septum per sample) containing $^{125}$I-PEO were soaked in saline solution. The samples were placed on a rotary shaker which allows a continuous shaking of the samples during the entire incubation period. Each set of tubes (in triplicate) was removed from the rotor torque after day-3. Each sample was counted for a total radioactivity before removal of saline solution, then it was washed with saline (1 ml×3). The washed piece was counted for the remaining radioactivity. The ratio between the remaining radioactivity of PEO-coated tubes after washing and the total radioactivity was recorded. Washed septums were reincubated with new saline solution for another 3 days, then 4 more days.

Results:

The results of regular PEO (PEO-OH), and amino-PEO (NH2-PEO)-coated septums are summarized in Table 18. All PEO-coated septums exhibit at least 10 fold lower fibrinogen binding than the corresponding uncoated septums (Table-19). The results of the stability of PEO-OH and PEO-NH2-coated septums are summarized in Table 20.

TABLE 18

Attachment Of $^{125}$I-PEOs onto Rubber Septums

| Type of PEO and coating concentrations | Bound-PEO (ug/mg septum) |
|---|---|
| PEO-OH-10% | 36 |
| PEO-OH-7.5% | 12 |
| PEO-OH-5.0% | 23 |
| NH2-PEO-7.5% | 9 |
| NH2-PEO-5.0% | 5 |
| NH2-PEO-2.5% | 8 |
| NH2-PEO-1.0% | 4 |

TABLE 19

Effect of PEO coatings on Fibrinogen binding on Septums.

| Type of PEO and coating concentrations | Bound-Fg ± SD, (ng/mg septum), (n = 3) |
|---|---|
| PEO-OH-20% | 0.78 ± 0.05 |
| PEO-OH-10% | 0.50 ± 0.03 |
| PEO-OH-5.0% | 0.74 ± 0.07 |
| NH2-PEO-7.5% | 0.5 ± 0.03 |
| NH2-PEO-5.0% | 0.79 ± 0.11 |
| NH2-PEO-2.5% | 0.90 ± 0.25 |
| Acrylate-PEO-7.5% | 3.06 ± 0.01 |
| Acrylate-PEO-5% | 2.16 ± 0.14 |
| Acrylate-PEO-2.5% | 2.45 ± 0.26 |
| Uncoated-septum | 16.42 ± 1.32 |

TABLE 20

Stability Of $^{125}$I-PEO-coated Septums in saline solution (% of recovery was calculated after each new replacement of saline solution)

| Type of PEO and coating concentrations | % recovery after Day-3 (1st saline) | % recovery after Day-3 (2nd saline) | % recovery after Day-4 (3rd saline) |
|---|---|---|---|
| PEO-OH-10% | 86 | 95 | 95 |
| PEO-OH-7.5% | 88 | 95 | 99 |
| PEO-OH-5.0% | 86 | 94 | 95 |
| NH2-PEO-7.5% | 47* | 104 | 108 |
| NH2-PEO-5.0% | 71 | 90 | 95 |
| NH2-PEO-2.5% | 101 | 95 | 94 |

*This low recovery may be due to the incomplete wash of unbound amino-PEO, especially at 7.5%, the NH2-PEO solution is very viscous.

It will be understood that various modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention is claimed as follows:

1. A medical device comprising:
    a body member that includes on a portion thereof a coating of a polyalkylene oxide that is coupled to a component selected from the group consisting of heparin, magainin, and chlorhexidine to form a coating.

2. The medical device of claim 1 wherein the coating includes water.

3. The medical device of claim 1 wherein the coating includes an additional functional group that provides a modified surface property to the coating.

4. The medical device of claim 1 wherein the device is a catheter.

5. The medical device of claim 1 wherein the device is a wound drain.

6. The medical device of claim 1 wherein the device is a guide wire.

7. The medical device of claim 1 wherein the device is a stent.

8. The medical device of claim 1 wherein the device is a chest tube.

9. The medical device of claim 1 wherein the device is a septum.

10. The medical device of claim 9 wherein the septum is made of a rubber.

11. The medical device of claim 1 wherein the portion thereof is constructed from silicone.

12. The medical device of claim 1 wherein the portion thereof is constructed from polyvinyl chloride.

13. A method of providing medical devices comprising the steps of:
   providing a medical device having a body; and
   coating using a one step process at least a portion of the body with a coating including a polyalkylene oxide derivative and a functional group to modify a surface property of the portion of the body.

14. The method of claim 13 including the step of providing a catheter as the medical device.

15. The method of claim 13 including the step of providing a wound drain as the medical device.

16. The method of claim 13 including the step of providing a chest tube as the medical device.

17. The method of claim 13 including the step of providing a guide wire as the medical device.

18. The method of claim 13 wherein the functional group is heparin.

19. The method of claim 13 including the step of providing a septum as the medical device.

20. A medical device comprising:
   a body member; and
   a coating thereon comprising a polyalkylene oxide that is coupled to a functional group that modifies a property of a surface of the body member.

21. The medical device of claim 20 wherein the polyalkylene oxide compound has the general structure Y-PEO-R-PEO-Y wherein Y is a reactive moiety selected from the group consisting of oxycarbonylimidazole; tresyl-, tosyl-, N-hydroxysuccinimidyl-, and p-nitrophenyl activated esters; acrylates; glycidyl ethers; amines; and aldehydes, wherein R is a spacer selected from compounds containing carbon, nitrogen, oxygen, and/or sulfur atoms, and wherein PEO is a high molecular weight polyalkylene oxide.

22. The medical device of claim 20 wherein the polyalkylene oxide compound has the general structure Y-PEO-Y wherein Y is a reactive moiety selected from the group consisting of oxycarbonylimidazole; tresyl-, tosyl-, N-hydroxysuccinimidyl-, and p-nitrophenyl activated esters; acrylates; glycidyl ethers; amines; and aldehydes.

23. The medical device of claim 20 wherein the functional group is heparin.

24. A method of coating a surface of a medical device with a copolymer and a compound that modifies the properties of the surface heparin comprising:
   placing a surface of a medical device in a polymer comprising an electrophilically active, polyalkylene oxide compound and a compound chosen from the group consisting of heparin, magainin, and chlorhexidine; and
   drying said polymer and compound onto said surface.

25. The medical device of claim 24 wherein the polyalkylene oxide compound has the general structure Y-PEOR-PEO-Y wherein Y is a reactive moiety selected from the group consisting of oxycarbonylimidazole; tresyl-, tosyl-, N-hydroxysuccinimidyl-, and p-nitrophenyl activated esters; acrylates; glycidyl ethers; amines; and aldehydes, wherein R is a spacer selected from compounds containing carbon, nitrogen, oxygen, and/or sulfur atoms, and wherein PEO is a high molecular weight polyalkylene oxide.

26. The medical device of claim 24 wherein the polyalkylene oxide compound has the general structure Y-PEO-Y wherein Y is a reactive moiety selected from the group consisting of oxycarbonylimidazole; tresyl-, tosyl-, N-hydroxysuccinimidyl-, and p-nitrophenyl activated esters; acrylates; glycidyl ethers; amines; and aldehydes.

* * * * *